(12) United States Patent
Hackbarth

(10) Patent No.: US 8,944,247 B2
(45) Date of Patent: Feb. 3, 2015

(54) POUCH-BASED CUMULATIVE PACKAGING

(75) Inventor: Ronald Hackbarth, Koblenz (DE)

(73) Assignee: LTS Lohmann Therapie Systeme AG, Andernach (DE)

( * ) Notice: Subject to any disclaimer, the term of this patent is extended or adjusted under 35 U.S.C. 154(b) by 0 days.

(21) Appl. No.: 12/300,194

(22) PCT Filed: Apr. 28, 2007

(86) PCT No.: PCT/EP2007/003786
§ 371 (c)(1),
(2), (4) Date: Nov. 10, 2008

(87) PCT Pub. No.: WO2007/131615
PCT Pub. Date: Nov. 22, 2007

(65) Prior Publication Data
US 2009/0158689 A1   Jun. 25, 2009

(30) Foreign Application Priority Data
May 12, 2006 (DE) .......................... 10 2006 022 198

(51) Int. Cl.
*A61B 17/06* (2006.01)
*B65D 85/00* (2006.01)
*B65D 83/08* (2006.01)
(Continued)

(52) U.S. Cl.
CPC .............. *B65D 83/08* (2013.01); *A61F 15/001* (2013.01); *B65D 75/5838* (2013.01); *B65D 75/5855* (2013.01); *B65D 77/02* (2013.01); *B65D 75/20* (2013.01)
USPC ............................ 206/440; 206/535; 206/425

(58) Field of Classification Search
USPC ......... 206/425, 440, 441, 449, 451, 493, 494, 206/535; 602/57, 58, 59; 53/157
See application file for complete search history.

(56) References Cited

U.S. PATENT DOCUMENTS 2,969,144 A * 1/1961 Zackheim ...................... 206/441
3,313,405 A * 4/1967 Blackford ...................... 206/441
(Continued)

FOREIGN PATENT DOCUMENTS

DE  1027844 B  4/1958
DE  9418312 U1  12/1995
(Continued)

OTHER PUBLICATIONS

International Preliminary Report on Patentability.

*Primary Examiner* — Anthony Stashick
*Assistant Examiner* — Kaushikkumar Desai
(74) *Attorney, Agent, or Firm* — Frommer Lawrence & Haug LLP

(57) ABSTRACT

The invention relates to a packaging unit (1), which comprises at least one agent-containing product (80), at least one main wrapping (30), and one secondary wrapping (10), wherein at least one agent-containing product (80) is stored sealed in each closed main wrapping (30), and wherein the main wrappings (30) are arranged in piles in the secondary wrapping (10) and are removably attached, at least in some regions, by means of perforation lines (38). Each main wrapping (30) of this is a sealed pouch with a gripping piece (70). The individual sealed pouch has a perforation seam (55) that bounds a tear-off region (47). The gripping piece (70) is joined to the tear-off region (47), opened by pulling a gripping piece (70), releases the agent-containing product (80). A further pulling of the gripping piece (70) separates the perforation line (38).

10 Claims, 4 Drawing Sheets

Figure 1:
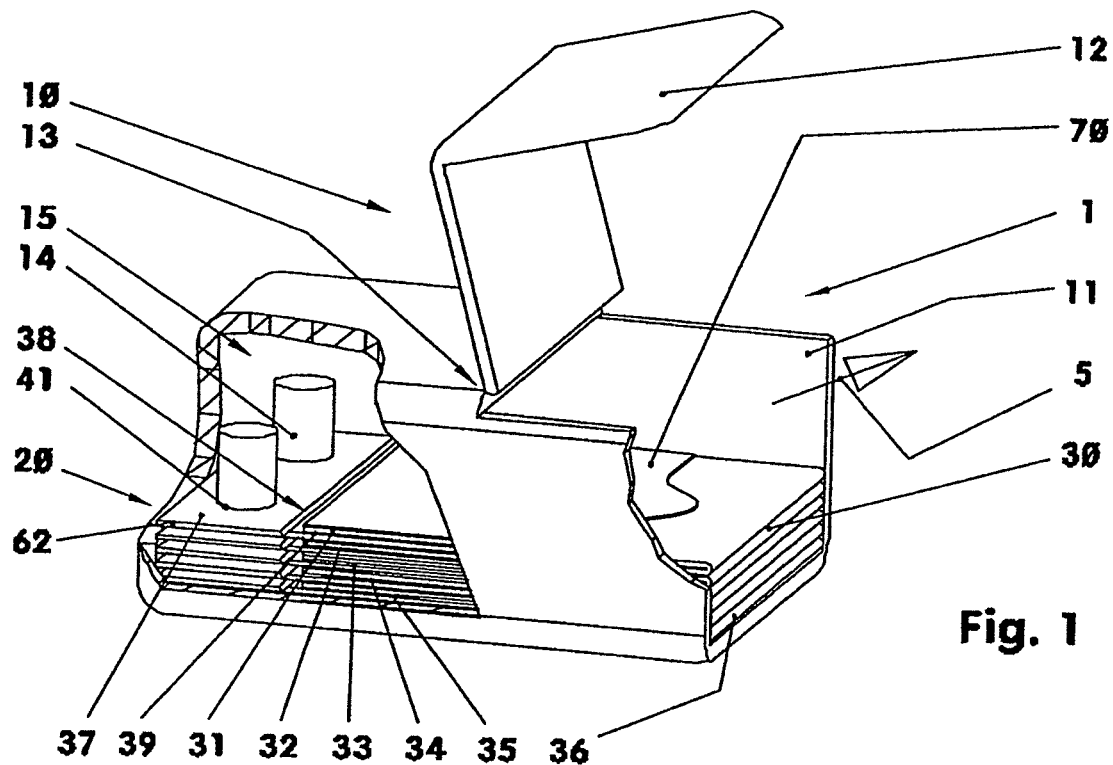

(51) Int. Cl.
*A61F 15/00* (2006.01)
*B65D 75/58* (2006.01)
*B65D 77/02* (2006.01)
*B65D 75/20* (2006.01)

(56) References Cited

U.S. PATENT DOCUMENTS

| | | | | |
|---|---|---|---|---|
| 3,520,403 | A * | 7/1970 | Moshel | 206/441 |
| 3,530,494 | A * | 9/1970 | Baratta | 206/441 |
| 3,677,866 | A * | 7/1972 | Pickett | 206/306 |
| 3,835,995 | A * | 9/1974 | Haines | 206/536 |
| 3,872,970 | A * | 3/1975 | Edison | 206/532 |
| 3,901,387 | A * | 8/1975 | Flynn | 206/525 |
| 4,194,624 | A | 3/1980 | Spiegelberg | |
| 4,243,144 | A * | 1/1981 | Margulies | 206/532 |
| 5,333,753 | A * | 8/1994 | Etheredge | 221/33 |
| 5,511,689 | A * | 4/1996 | Frank | 221/73 |
| 6,124,522 | A * | 9/2000 | Schroeder | 602/57 |
| 6,140,549 | A * | 10/2000 | Pompei, Jr. | 602/57 |
| 6,708,826 | B1 * | 3/2004 | Ginsberg et al. | 206/535 |
| 6,974,032 | B2 * | 12/2005 | Intini | 206/532 |
| 7,004,321 | B1 | 2/2006 | Palm et al. | |
| 7,188,729 | B2 * | 3/2007 | DeJonge | 206/535 |
| 7,357,255 | B2 * | 4/2008 | Ginsberg et al. | 206/535 |
| 7,506,760 | B2 * | 3/2009 | Grossman | 206/440 |
| 2002/0064619 | A1* | 5/2002 | Schroeder | 428/40.1 |
| 2005/0218201 | A1* | 10/2005 | Billig et al. | 229/122 |
| 2009/0158689 | A1* | 6/2009 | Hackbarth | 53/157 |

FOREIGN PATENT DOCUMENTS

| | | |
|---|---|---|
| EP | 0 101 298 | 2/1984 |
| EP | 0 101298 A2 | 2/1984 |
| EP | 0177555 B1 | 1/1989 |
| EP | 0948949 A | 10/1999 |
| EP | 1161375 B1 | 12/2001 |
| WO | WO 03/062076 | 7/2003 |

* cited by examiner

POUCH-BASED CUMULATIVE PACKAGING

The invention relates to a packaging unit, which comprises at least one active-substance-containing product, at least one primary packaging and a secondary packaging, wherein at least one active-substance-containing product is stored sealed in each closed primary packaging, and wherein the primary packagings are arranged stacked in the secondary packaging and are secured releasably, at least in some areas, by means of predetermined partition lines.

EP 1 161 375 B1 discloses a packaging unit of this kind. The individual primary packagings are removed from the secondary packaging in a predetermined sequence. After their removal, the individual primary packagings are opened, and the respective active-substance-containing product is removed. The active-substance-containing products may be damaged when doing so. In addition, the primary packagings may be removed and left unopened and, for example, may be opened by children when unsupervised.

The object of the present invention is therefore to develop a packaging unit in which the active-substance-containing products are packaged in a childproof manner and can be easily removed without any particular risk of being damaged.

This object is achieved by the features of the main claim. To this end, each primary packaging is a sealed pouch with a gripping piece. The individual sealed pouch has a predetermined partition seam that delimits a tear-open area. The gripping piece is connected to the tear-open area. The tear-open area, opened by pulling the gripping piece, exposes the active-substance-containing product. A further pulling of the gripping piece separates the predetermined partition line.

In order to remove the active-substance-containing products, it is therefore necessary to tear open the individual primary packaging secured in the secondary packaging. Only then can the primary packaging be separated from the secondary packaging. The childproof safety cannot be circumvented in the sense of the primary packagings being removed unopened from the secondary packaging and stored outside of the secondary packaging.

Further details of the invention are set forth in the dependent claims and in the following description of schematically illustrated embodiments.

Figure 2:
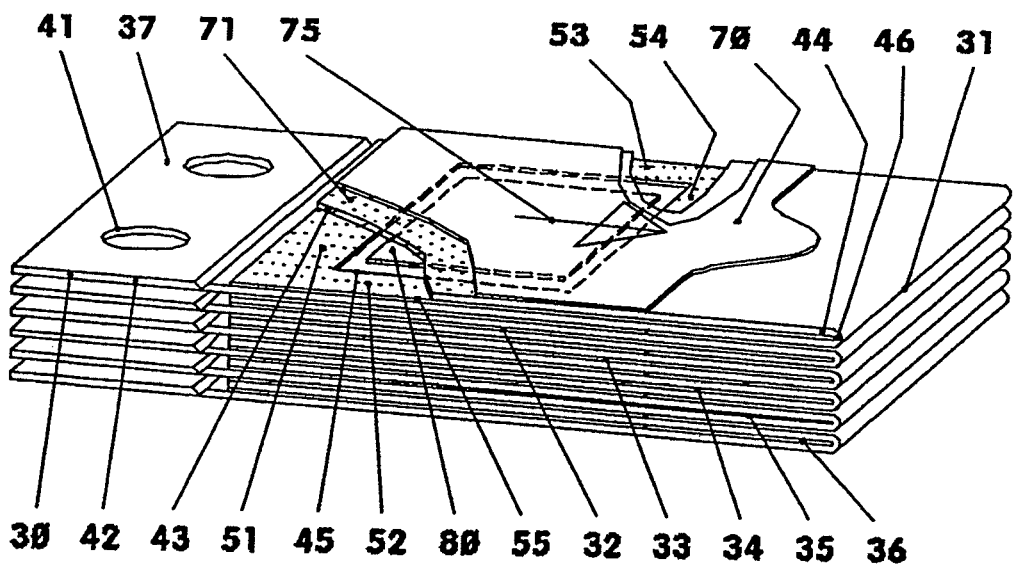
Figure 3:
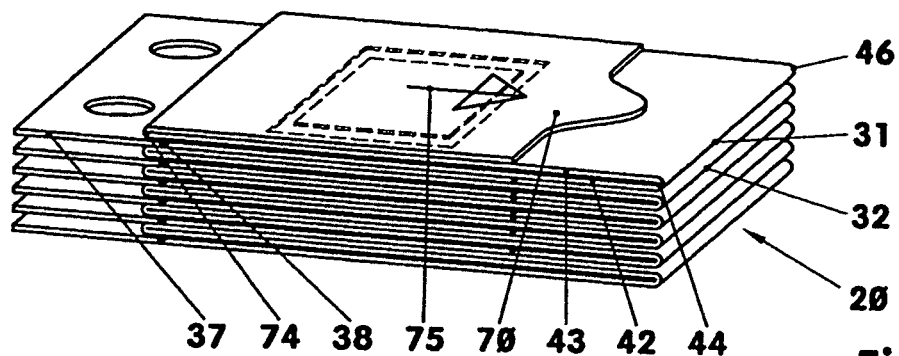
Figure 4:
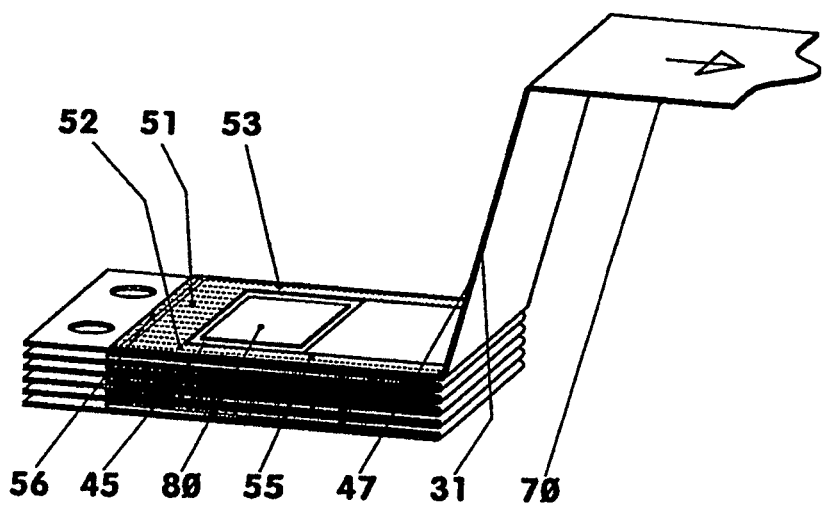
Figure 5:
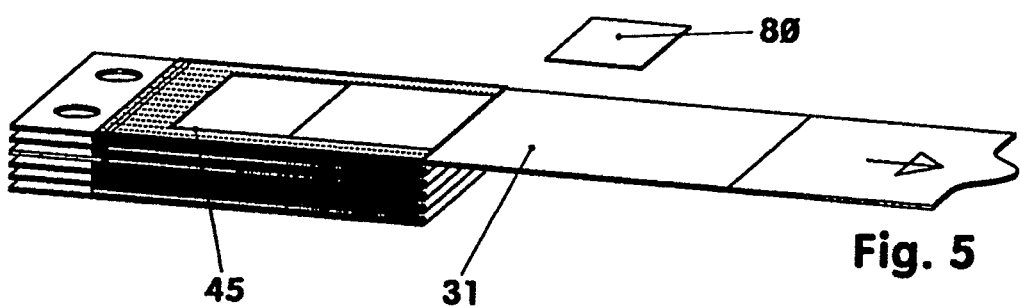
Figure 6:
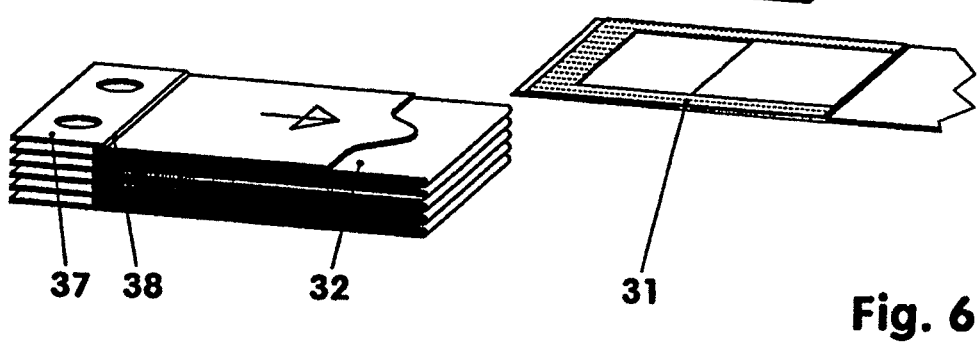
Figure 7:
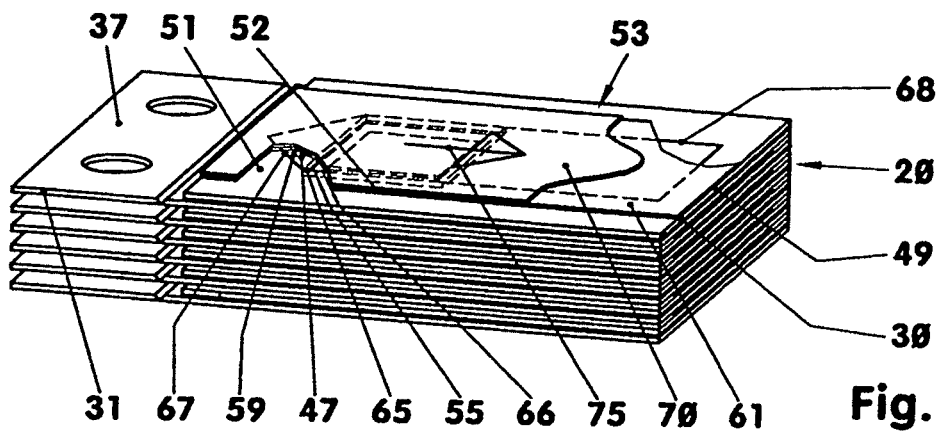
Figure 8:
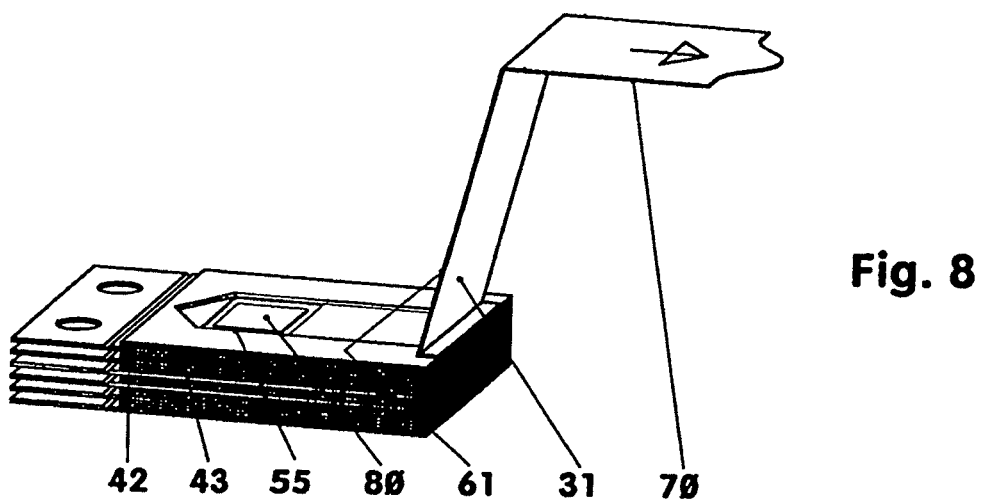
Figure 9:
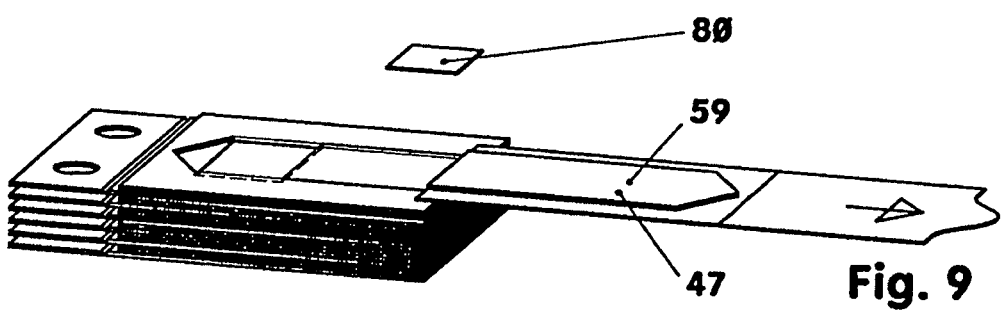
Figure 10:
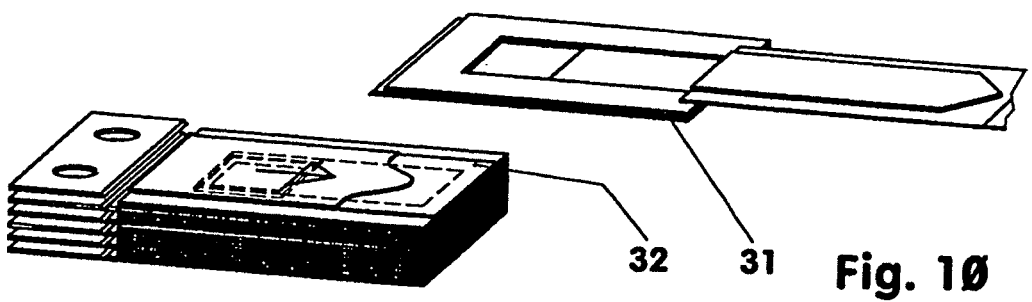
Figure 11:
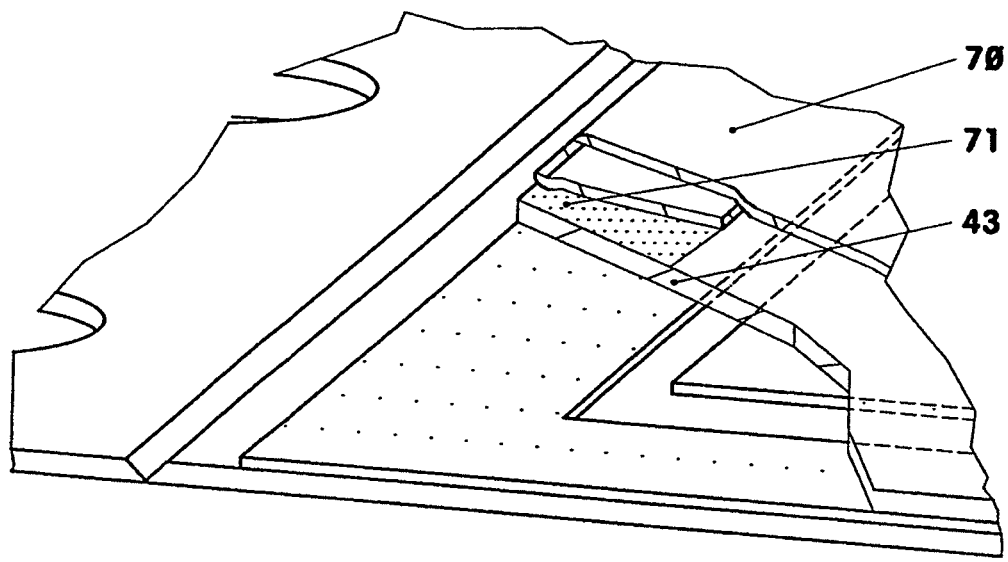
Figure 12:
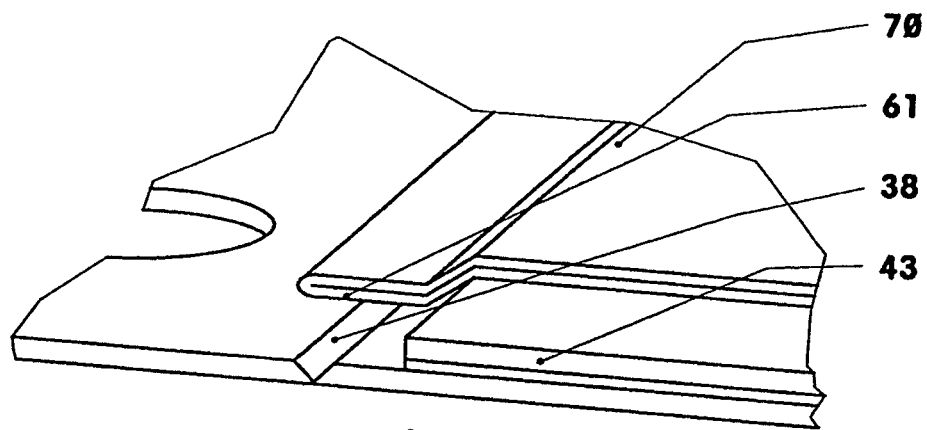
Figure 13:
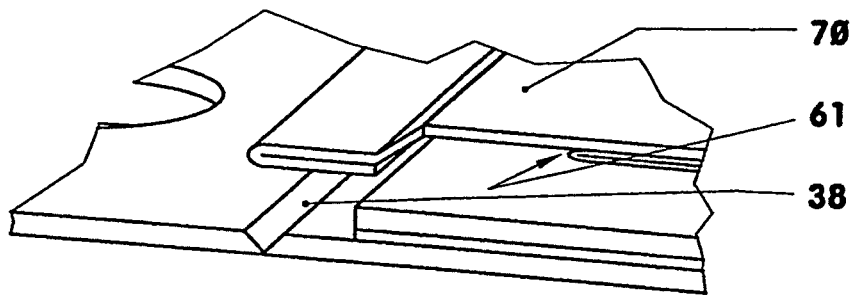

FIG. 1: packaging unit;
FIG. 2: stack of pouches from FIG. 1;
FIG. 3: stack of closed primary packagings;
FIG. 4: stack with an opened primary packaging;
FIG. 5: stack after removal of an active-substance-containing product;
FIG. 6: stack with a separated primary packaging;
FIG. 7: stack of four-edge sealed pouches;
FIG. 8: stack from FIG. 7 with an opened primary packaging;
FIG. 9: stack from FIG. 7 after removal of an active-substance-containing product;
FIG. 10: stack from FIG. 7 with a separated primary packaging;
FIG. 11: stack from FIG. 2 with folded gripping piece;
FIG. 12: stack from FIG. 7 with securing of the predetermined partition line;
FIG. 13: stack from FIG. 7 with a gripping piece that secures the predetermined partition line and the predetermined partition seam.

FIG. 1 shows a packaging unit (1). The latter is a cumulative packaging (1) in which primary packagings (30) with active-substance-containing products (80) are arranged stacked in a secondary packaging (10).

The secondary packaging (10) is, for example, a cuboid box. It comprises, for example, a housing (11) and a fold-open lid (12). In this illustrative embodiment, the lid (12) is connected to the housing (11) by means of a film hinge (13). The lid (12) can also be designed as a sliding lid, a removable lid, etc. The closure of this secondary packaging (10) has, for example, a childproof safety feature (not shown here). The corners and edges of the box (10) are rounded, for example. With the lid (12) closed, the box (10) is substantially sealed off against entry of foreign substances, for example. If appropriate, additional sealing elements can be arranged on the lid (12) and/or on the housing (11) in order to hermetically seal the box (10) at least during storage.

A stack (20) of primary packagings (30) is secured releasably in the interior (15) of the box (10). The primary packagings (30) are, for example, sealed pouches (30) which have been sealed off hermetically, and in a manner impermeable to odors, and which each have a gripping piece (70). The pouches (30) are locked in the box (10) by means of two studs (14). The studs (14) extend through the pouches (30) via two through-holes (41), which are at a considerable distance here from the outer edges (62) of the pouches (30). Instead of the two studs (14) shown, a single stud, a clip, etc., can be provided to lock the pouches (30) in the box (10). Other types of force-fit and/or form-fit securing are also conceivable. In the cumulative packaging (1) shown in FIG. 1, for example, six primary packagings (31-36) are provided. The pouch (31) is the uppermost pouch in the stack (20), while the pouch (36) is the lowermost of the stacked pouches (31-36).

In each primary packaging (31-36), there is, for example, exactly one active-substance-containing product (80), cf. FIG. 2. The active-substance-containing products (80) are, for example, thin and flexible single-layer or multiple-layer laminas. These can be, for example, transdermal therapy systems, wafers, aroma tablets, indicator strips or tablets, etc. They contain, for example, readily volatile active substances that require a hermetically sealed primary packaging (30). The active-substance-containing products (80) lie in product nests (45) of the pouches (30). These product nests (45) are larger than the tablets (80) placed in them. Different active-substance-containing products (80) can be stored in the individual pouches (30) of a cumulative packaging (1), with suitable identification. It is also conceivable for several active-substance-containing products (80) to be arranged in one pouch (30).

The individual pouch (30), cf. FIG. 2, is composed of several layers of interconnected packing materials (42, 43). These packing materials (42, 43) are, for example, gas-impermeable plastic films produced from webs of packing material. The packing materials (42, 43) are, for example, designed to be impermeable to odor, water and/or oxygen. The individual pouch (30) has a securing area (37), which engages round the studs (14), and a receiving area (39), which comprises the product nest (45) with the active-substance-containing product (80). The two areas (37, 39) are connected to each other at a predetermined partition line (38), e.g. a perforation. This perforation (38) lies transverse to the direction of removal (5) of the pouches (30) from the box (10). Instead of being designed as perforation (38), the predetermined partition line (38) can also be prepared by means of scoring by laser, punching, scratching, etc.

The sealed pouches (30) shown in FIGS. 1 and 2 are each composed of a lower packing material (42), an upper packing material (43) and a gripping piece (70). The upper packing material (43) and the lower packing material (42) form part of an asymmetrically folded, rectangular packing material web (44). Here, the lower packing material (42) is longer than the upper packing material (43). The lower packing material (42) comprises the securing area (37) and the predetermined partition line (38). The fold (46), which connects the upper packing material (43) and the lower packing material (42) non-releasably to each other, lies at that end of the pouch (30) directed away from the securing area (37).

The upper packing material (43) and the lower packing material (42) are, for example, sealed together at four releasable sealed seams (51-54). Here, two longitudinal seams (52, 53) delimit the two longitudinal sides of the product nest (45), and two transverse seams (51, 54) delimit the transverse sides thereof. Instead of being designed as a four-edge sealed pouch, this pouch (30) can also be designed as a three-edge sealed pouch, in which case the transverse seam (54) on the fold (46) is then omitted. The pouch (30) can be made shorter in this way. The other transverse seam (51) can cover the predetermined partition line (38), such that the upper packing material (43) is connected to the lower packing material (42) both in the securing area (37) and also in the receiving area (39), cf. FIG. 3. The individual stacked pouches (31-36) can be connected to one another in the securing area (37).

The four-edge sealed pouch (30) can also be designed such that the upper packing material (43) and the lower packing material (42) are not connected by means of a fold (46). The transverse seam (51) and the longitudinal seams (52, 53) are then designed as seams that can be separated, whereas the transverse seam (54) is a non-separable seam.

In this illustrative embodiment, the gripping piece (7) is sealed non-releasably onto the upper packing material (43) at a transverse seam (71). The gripping piece (70) can also be part of the packing material web (44) and, for example, can be produced by doubling the upper packing material (43). Sealing and doubling on the upper packing material (43) is also conceivable, cf. FIG. 11. The gripping piece (70) in the illustrative embodiment is composed, for example, of a plastic film which is half as thick as the packing materials (42, 43). However, it can also be produced from the same substance as the packing materials (42, 43). The length of the gripping piece (70) is, for example, two thirds of the length of the upper packing material (43). The transverse seam (71) or the fold between the upper packing material (43) and the gripping piece (70) can overlap the predetermined partition line (38).

If an active-substance-containing product (80) is to be removed, the lid (12) is first opened. The user sees the stack (20) of pouches (30), the gripping piece (70) of the uppermost pouch (31) being visible. The area of the sealed seam (51) is completely concealed in the box (10).

The removal of an active-substance-containing product (80) is now described with reference to FIGS. 3 to 6, in which the stack (20) of peel-open pouches (31-36) is shown without the secondary packaging (10). Here, the stack (20) is shown enlarged in FIG. 3 compared to FIGS. 4-6. The three-edge sealed pouches (31-36) shown in FIGS. 3-6 are each produced from a single packing material web (44). The upper packing material (43) abuts the lower packing material (42) in the fold (46). The gripping piece (70) initially lies on the upper packing material (43), cf. FIG. 3, and is connected non-releasably to it by means of a further transverse fold (74). The upper packing material (43) overlaps the predetermined partition line (38).

The upper packing material (43) and the lower packing material (42) are connected to each other by means of two longitudinal seams (52, 53) and a transverse seam (51), cf. FIG. 4. All of these seams (51-53) are sealed seams that can be separated. The longitudinal seams (52, 53) are arranged on both sides of the optionally recessed product nest (45). The transverse seam (51) lies on both sides of the predetermined partition line (38) and covers parts of the securing area (37) and also parts of the receiving area (39). If appropriate, an area of the gripping piece (70) designed as a narrow strip adjoining the fold (74), and parallel thereto, can also be sealed releasably onto the upper packing material (43). In this way, the position of the gripping piece (70) is fixed during storage of the box (10). Only very low forces are needed to release this seam.

To open the uppermost peel-open pouch (31), the user pulls the gripping piece (70) in the direction of the for example engraved arrow (75). Depending on the design of the box (10), he can pull the gripping piece (70) at a steep or shallow pull-off angle. The optionally present seam or the adhesive area between the gripping piece (70) and the upper packing material (43) is first separated. Upon further pulling, the upper packing material (43) is peeled off from the lower packing material (42) along the predetermined partition seam (55), cf. FIG. 4. In this illustrative embodiment, the predetermined partition seam (55) comprises the separable sealed seams (51-53). It delimits the tear-open area (47) of the peel-open pouch (31). Here, the transverse seam (51), which overlaps the predetermined partition line (38), prevents separation of the perforation (38) when the peel-open pouch (31) is closed. As the upper packing material (43) is pulled off, the tear-open area (47) of the peel-open pouch (30) is opened. The active-substance-containing product (80) is exposed over its full surface area. It can now be easily taken hold of by the fingers and can then be removed from the product nest (45). There is no risk here of the thin and flexible lamina (80) being damaged, even when it is only a few tenths of a millimeter thick.

Upon further pulling of the gripping piece (70), the now empty peel-open pouch (31) is now stretched, cf. FIG. 5. The tear-open area (47) is now completely opened. The separable sealed seams (51-53) are separated.

In order to close the box (10) after the active-substance-containing product (80) has been removed, the empty pouch (31) first has to be removed. For this purpose, the perforation (38) is separated, for example by a tug on the gripping piece (70), cf. FIG. 6. Since the securing area (56) formed by the transverse seam (51) is already separated, the force needed to separate the perforation (38) is, for example, the same as the force for peeling open the three-edge sealed pouch (31). The empty, opened pouch (31) can now be disposed of. The user sees, in the box (10), the next closed pouch (32) with its gripping piece (70).

The box (10), which is childproof, for example, can now be closed again and stored in a safe place. To remove, for example, the next dose of medication, the user can use the next gripping piece (70) to tear open the next pouch (32) when the box (10) is opened.

If appropriate, it is also possible for the active-substance-containing product (80) to be removed from the product nest (45) only after the opened pouch (31) has been torn off. For this purpose, the product nest (45) can have a safety edge that prevents the active-substance-containing product (80) from falling out during the tearing-off of the pouch (31).

With this packaging unit (1), the active-substance-containing product (80) can be removed safely and free of damage. Only opened pouches (30) can be removed from the secondary packaging (10). This ensures that no pouches (30) are removed to be kept "in reserve" and then stored in a place accessible to children, for example.

In FIGS. 7-10, a four-edge sealed pouch (30) in the form of a tear-open pouch is depicted as the primary packaging (30) for the active-substance-containing products. In FIG. 7, the stack (20) of pouches (31-36) is shown enlarged compared to FIGS. 8-10. Each of these pouches (31-36) also comprises an upper packing material (43) and a lower packing material (42). These two packing materials (42, 43) are connected to each other by means of two longitudinal seams (52, 53) and two transverse seams (51, 54) that delimit the product nest (45), cf. FIG. 2. These sealed seams (51-54) are not peelable and cannot therefore be separated. The sealed pouch (30) shown in FIGS. 7-10 can also be designed as a three-edge sealed pouch (30). In this case, the upper packing material (43) is connected non-releasably to the lower packing material (42), for example by means of a fold (46).

The upper packing material (43) is mechanically weakened along a line (65), cf. FIG. 7. This line (65) has three portions (66-68). Two mutually parallel portions (66, 68) are in alignment, for example, with the lateral limits of the product nest (45) and are guided as far as the transverse seam (54) in the direction of the arrow (75) on the gripping piece (70). A further portion (67) of this line (65) connects these two line portions (66, 68). It forms a tip (67) oriented in the direction of the securing area (37). This tip (67) lies between the product nest (45) and the securing area (37). Inside the area enclosed by the line (65), the upper packing material (43) and the lower packing material (42) are not sealed together. The mechanical weakening is, for example, a score produced by means of a laser. The upper strata of the packing material (43) are thus removed, without damaging the lower strata of the packing material (43), which are responsible for the sealing of the pouch (30). The area of the packing material (43) delimited by the line (65) is designated hereinafter as tear-open piece (59).

A cover piece (61) is partially sealed non-releasably onto the tear-open piece (59). The cover piece (61) overlaps the tear-open piece (59) and protrudes on both longitudinal sides by half the width of a sealed seam (52, 53), for example. Its length corresponds, for example, to the length of the upper packing material (43). At its end oriented in the direction of the securing area (37), the cover piece (61) has the gripping piece (70) sealed onto it, for example with a non-separable sealed seam (71), cf. FIG. 11. The cover piece (61) can also be folded at the side directed toward the securing area (37) in order to form the gripping piece (70). In this illustrative embodiment too, the gripping piece (70) bears a marking (75), in order to identify the direction of removal (5) of the pouches (30). The gripping piece (70) can additionally be connected to the cover piece (61) by means of a seam or by means of an adhesive area.

The first pouch (31) is opened in a manner analogous to the opening of the pouch (31) shown in FIGS. 3-6. The gripping piece (70) is pulled by the fingers in the direction indicated by the marking arrow (75). In doing so, the gripping piece (70) pulls the cover piece (61) with it. The cover piece (61) in turn tears the tear-open piece (59) from the upper packing material (43), starting from the tip (67), along the predetermined partition seam (55) marked by the line (65). The now opened tear-open area (47) now exposes the full surface area of the active-substance-containing product (80) in the product nest (45), cf. FIG. 8. The active-substance-containing product (80) can now be removed without damage. In this embodiment too, the predetermined partition line (38) can be additionally protected, for example by a separable sealing of the cover piece (61) on the securing area (37), cf. FIG. 12.

Upon further pulling of the gripping piece (70), the tear-open piece (59) is torn open as far as the end of the line (65). The transverse seam (54) prevents further tearing open. After this, the pulling force is transmitted to the perforation (38). The pouch (31), which is now empty, for example, is torn off along the perforation (38), for example by means of a short, forceful tug. After the first opened pouch (31) has been removed, only closed pouches (32-36) remain in the box (10), each of them holding an active-substance-containing product (80). These pouches (32-36) can be removed by the same technique.

It is thus ensured that there can be no unopened pouches (30) outside the box (10).

The gripping piece (70) can also be designed such that it covers both the predetermined partition line (38) and also the cover piece (61), cf. FIG. 13. When the gripping piece (70) is pulled, the predetermined partition seam (55) is then opened and the predetermined partition line (38) exposed.

LIST OF REFERENCE NUMBERS 1 packaging unit, cumulative packaging
5 direction of removal
10 secondary packaging, container, box
11 housing
12 lid
13 film hinge
14 stud
15 interior
20 stack
30 primary packaging, sealed pouch
31-36 primary packagings, sealed pouches
37 securing area
38 predetermined partition line, perforation
39 receiving area
41 through-holes
42 lower packing material
43 upper packing material
44 web of packing material
45 product nest
46 fold
47 tear-open area
49 edge of (43)
51 sealed seam, transverse seam
52 sealed seam, longitudinal seam
53 sealed seam, longitudinal seam
54 sealed seam, transverse seam
55 predetermined partition seam
56 securing area
59 tear-open piece
61 cover piece
62 outer edges
65 line
66 portion of (65)
67 portion of (65), tip
68 portion of (65)
70 gripping piece
71 transverse seam
74 fold
75 marking, arrow
80 active-substance-containing product, wafer

The invention claimed is:

1. A packaging unit, which comprises
a plurality of primary packagings; and
a secondary packaging;
wherein at least one active-substance-containing product is stored sealed in each closed primary packaging;
wherein each primary packaging is arranged stacked in the secondary packaging and is secured releasably, at least in one area, by a predetermined partition line;
wherein each primary packaging comprises a lower packing material comprising a securing area at one side of the primary packaging;

wherein, at another side of each primary packaging, the lower packing material is connected with an upper packing material;

wherein, a gripping piece is part of the upper packing material;

wherein each primary packaging has a receiving area which comprises a recessed product nest with the active-substance-containing product;

wherein the upper packing material and lower packing material are connected to each other to seal the recessed product nest by means of two longitudinal seams and a transverse seam, where the longitudinal seams are arranged on both sides of the recessed product nest;

wherein the secondary packaging comprises a cuboid box which includes a housing and a fold-open lid;

wherein the upper packing material and the lower packing material are connected inseparably to each other at least on a side of the sealed primary packaging directed away from the predetermined partition line; and wherein the transverse seam overlaps the predetermined partition line, preventing separation of the predetermined partition line when the sealed primary packaging is not opened so that the primary packaging cannot be separated from the secondary packaging until the primary packaging is opened to reveal the recessed product nest and the active-substance-containing product.

2. The packaging unit as claimed in claim 1;
wherein the active-substance-containing product is configured to be exposed over the whole surface area of the active-substance-containing product.

3. The packaging unit as claimed in claim 1;
wherein the predetermined partition line has perforations.

4. The packaging unit as claimed in claim 1;
wherein the sealed primary packagings are secured with a form fit and/or force fit in the secondary packaging.

5. The packaging unit as claimed in claim 1;
wherein the predetermined partition lines of the sealed primary packagings include:
   at least one transverse seam sealed such that it can be separated; and
   two longitudinal seams oriented in the direction of pulling of the gripping piece and sealed such that they can be separated, said longitudinal seams delimiting the product nest.

6. The packaging unit as claimed in claim 1;
wherein at least the sealed seams delimiting the product nest are sealed seams that cannot be separated.

7. The packaging unit as claimed in claim 6;
wherein the upper packing material comprises a tear-open piece which is connected inseparably to the gripping piece.

8. The packaging unit as claimed in claim 1;
wherein the predetermined partition line is connected with a securing portion securing the primary package to the secondary package.

9. The packaging unit as claimed in claim 1;
wherein the upper packing material and the lower packing material are configured to be asymmetrically folded.

10. The packaging unit as claimed in claim 1;
wherein the recessed product nest comprises a recessed area formed in at least one of the upper and lower packaging materials.

* * * * *